United States Patent
Omoya (10) Patent No.: US 9,547,270 B2
(45) Date of Patent: Jan. 17, 2017

(54) IMAGE FORMING APPARATUS AND ABNORMALITY DETECTION APPARATUS AND METHOD FOR HUMIDITY SENSOR DEVICE

(71) Applicant: KYOCERA Document Solutions Inc., Osaka (JP)

(72) Inventor: Shinichi Omoya, Osaka (JP)

(73) Assignee: KYOCERA Document Solutions Inc., Osaka (JP)

(*) Notice: Subject to any disclaimer, the term of this patent is extended or adjusted under 35 U.S.C. 154(b) by 400 days.

(21) Appl. No.: 14/226,862

(22) Filed: Mar. 27, 2014

(65) Prior Publication Data

US 2014/0292352 A1  Oct. 2, 2014

(30) Foreign Application Priority Data

Mar. 28, 2013  (JP) .................... 2013-070318

(51) Int. Cl.
*G01N 27/02* (2006.01)
*G03G 15/00* (2006.01)
*G01N 27/12* (2006.01)
*G03G 21/20* (2006.01)

(52) U.S. Cl.
CPC ............ *G03G 15/55* (2013.01); *G01N 27/121* (2013.01); *G03G 15/50* (2013.01); *G03G 21/20* (2013.01)

(58) Field of Classification Search
CPC ........ G03G 15/55; G03G 15/50; G03G 21/20; G01N 27/121
See application file for complete search history.

(56) References Cited

U.S. PATENT DOCUMENTS

| 7,597,001 B2 | 10/2009 | Hayakawa |
| 2007/0186650 A1* | 8/2007 | Hayakawa ............ G03G 15/55 73/335.05 |

FOREIGN PATENT DOCUMENTS

| JP | 07-285320 A | 10/1995 |
| JP | 2003-166964 A | 6/2003 |
| JP | 2007-248455 A | 9/2007 |

* cited by examiner

*Primary Examiner* — David Gray
*Assistant Examiner* — Michael Harrison
(74) *Attorney, Agent, or Firm* — Studebaker & Brackett PC (57) ABSTRACT

An image forming apparatus includes a humidity sensor element, a resistor, a clock supply section, a detection section and a determination section. The detection section detects a humidity on the basis of a divided voltage value obtained by the humidity sensor element and the resistor. The determination section acquires the divided voltage value at a first timing within a period from a rising edge to a falling edge of a first clock signal and at a second timing within a period from a falling edge to a rising edge of the first clock signal, and determines, on the basis of the divided voltage values thus acquired, whether or not the humidity detected by the detection section is normal.

9 Claims, 4 Drawing Sheets

FIG. 5

IMAGE FORMING APPARATUS AND ABNORMALITY DETECTION APPARATUS AND METHOD FOR HUMIDITY SENSOR DEVICE

INCORPORATION BY REFERENCE

The present application claims priority under 35 U.S.C. §119 to Japanese Patent Application No. 2013-070318, filed on Mar. 28, 2013. The contents of this application are incorporated herein by reference in their entirety.

BACKGROUND

The present disclosure relates to an image forming apparatus, and an abnormality detection apparatus and an abnormality detection method for a humidity sensor device.

An image forming apparatus such as a printer, a copying machine or a multifunction peripheral may be provided with a humidity sensor. For example, the humidity sensor is used for detecting humidity in order to keep the quality of image formation constant by controlling the charge amount of a photoconductive drum or the like in accordance with the change of ambient humidity. The humidity sensor may be, however, damaged by deterioration over time or the like. Therefore, a method or an apparatus for detecting a malfunction of the humidity sensor has been proposed.

For example, an image forming apparatus including a humidity sensor element, a resistor, a signal output section and a measurement section has been proposed. In an example of such an image forming apparatus, the resistance value of the humidity sensor element is varied in accordance with humidity change. The resistor is serially connected to the humidity sensor element. The signal output section outputs a clock signal (for example, with a frequency of 1 kHz and a pulse time width of 500 μs) to the humidity sensor element and the resistor. The measurement section detects a voltage on a node between the humidity sensor element and the resistor at a timing precedently determined based on a rising edge or a falling edge of the clock signal (for example, 250 μs after a rising or falling edge), and obtains a humidity on the basis of the value of the detected voltage. In accordance with the detected voltage, the measurement section detects a voltage at a timing different from the precedently determined timing (for example, 50 μs after a rising or falling edge). Thus, abnormality of the humidity sensor element can be detected.

Alternatively, a humidity sensor controller for detecting deterioration of a humidity sensor by comparing a sensor output of the humidity sensor with a sensor output of a normal humidity sensor has been disclosed. Besides, an air conditioner for a vehicle that detects a malfunction caused by characteristic deterioration of a humidity sensor depending upon whether or not a humidity detection signal is varied in a state where the humidity in the vehicle is varied (as, for example, immediately after starting a dehumidifying operation) has been disclosed.

SUMMARY

An image forming apparatus according to the present disclosure includes: a humidity sensor element having a first terminal and a second terminal and configured to vary, in accordance with humidity change, an electric resistance value between the first terminal and the second terminal; a resistor having a third terminal and a fourth terminal, with the third terminal serially connected to the second terminal, and having a prescribed electric resistance between the third terminal and the fourth terminal; a clock supply section configured to supply a first clock signal to the first terminal and a second clock signal having an opposite phase to the first clock signal to the fourth terminal; a detection section configured to detect a humidity on the basis of a divided voltage value obtained by the humidity sensor element and the resistor; and a determination section configured to acquire the divided voltage value at a first timing within a period from a rising edge to a falling edge of the first clock signal and at a second timing within a period from a falling edge to a rising edge of the first clock signal, and to determine, on the basis of the divided voltage value acquired at the first timing and the divided voltage value acquired at the second timing, whether or not the humidity detected by the detection section is normal.

An abnormality detection apparatus for a humidity sensor device according to the present disclosure detects whether or not the humidity sensor device has abnormality. The humidity sensor device includes: a humidity sensor element having a first terminal and a second terminal and configured to vary, in accordance with humidity change, an electric resistance value between the first terminal and the second terminal; a resistor having a third terminal and a fourth terminal, with the third terminal serially connected to the second terminal, and having a prescribed electric resistance between the third terminal and the fourth terminal; a clock supply section configured to supply a first clock signal to the first terminal and a second clock signal having an opposite phase to the first clock signal to the fourth terminal; and a detection section configured to detect a humidity on the basis of a divided voltage value obtained by the humidity sensor element and the resistor. The abnormality detection apparatus for a humidity sensor device according to the present disclosure includes a determination section configured to acquire the divided voltage value at a first timing within a period from a rising edge to a falling edge of the first clock signal and at a second timing within a period from a falling edge to a rising edge of the first clock signal, and to determine, on the basis of the divided voltage value acquired at the first timing and the divided voltage value acquired at the second timing, whether or not the humidity detected by the detection section is normal.

An abnormality detection method for a humidity sensor device according to the present disclosure detects whether or not the humidity sensor device has abnormality. The humidity sensor device includes: a humidity sensor element having a first terminal and a second terminal and configured to vary, in accordance with humidity change, an electric resistance value between the first terminal and the second terminal; a resistor having a third terminal and a fourth terminal, with the third terminal serially connected to the second terminal, and having a prescribed electric resistance between the third terminal and the fourth terminal; a clock supply section configured to supply a first clock signal to the first terminal and a second clock signal having an opposite phase to the first clock signal to the fourth terminal; and a detection section configured to detect a humidity on the basis of a divided voltage value obtained by the humidity sensor element and the resistor. The abnormality detection method for a humidity sensor device includes: acquiring the divided voltage value at a first timing within a period from a rising edge to a falling edge of the first clock signal; acquiring the divided voltage value at a second timing within a period from a falling edge to a rising edge of the first clock signal; and determining, on the basis of the divided voltage value acquired at the first timing and the divided voltage value acquired at the second timing, whether or not the humidity detected by the detection section is normal.

DETAILED DESCRIPTION

Now, one embodiment of the present disclosure will be described with reference to the accompanying drawings.

Figure 1:
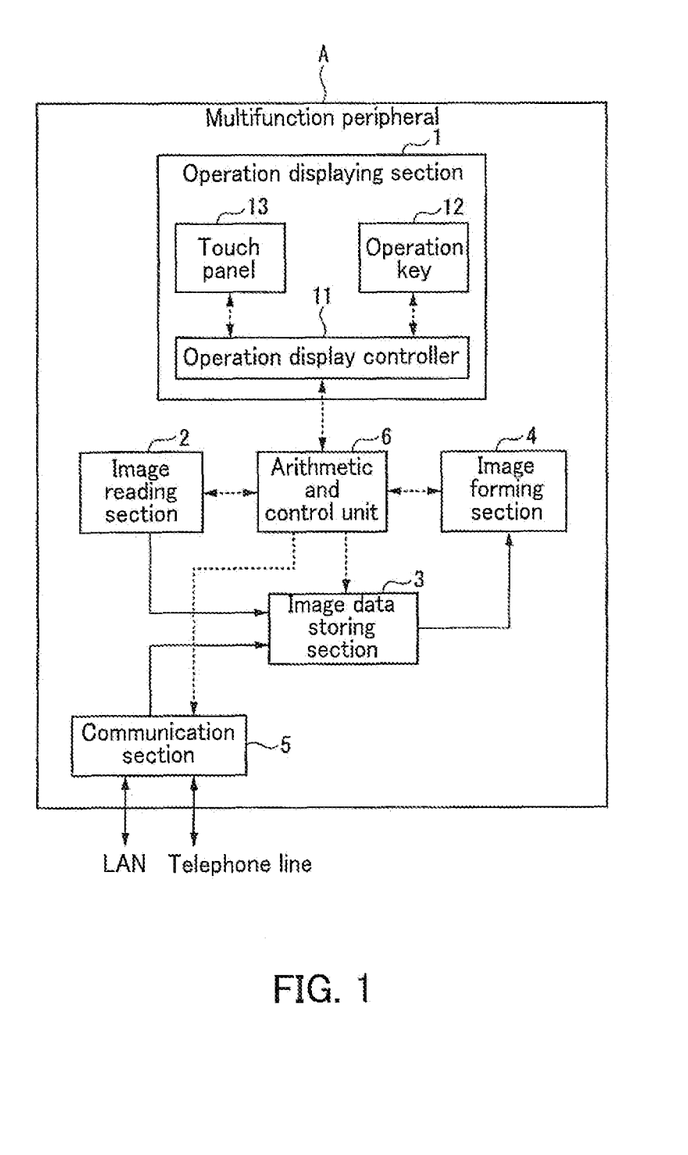
FIG. 1 is a functional block diagram of a multifunction peripheral according to an embodiment of the present disclosure.

A multifunction peripheral A according to the present embodiment is an image forming apparatus for electrographically forming an image on recording paper. As illustrated in FIG. 1, the multifunction peripheral A includes an operation displaying section 1, an image reading section 2, an image data storing section 3, an image forming section 4, a communication section 5, and an arithmetic and control unit 6 (corresponding to a determination section and a clock generation circuit). Incidentally, in FIG. 1, each solid arrow indicates the flow of data and each broken arrow indicates the flow of a control signal or a detection signal.

The operation displaying section 1 includes an operation display controller 11, an operation key 12, that is, a hardware key, and a touch panel 13 for displaying various images. The operation displaying section 1 functions as a man-machine interface for correlating a user with the multifunction peripheral A.

The operation display controller 11 is a control device for controlling the operation key 12 and the touch panel 13 on the basis of an instruction (a control signal) output by the arithmetic and control unit 6. The operation display controller 11 includes a processor, an internal memory and an interface circuit. The interface circuit is electrically connected to the operation key 12 and the touch panel 13 so as to transmit/receive signals to/from the operation key 12 and the touch panel 13. The operation display controller 11 controls the whole operation of the operation displaying section 1 on the basis of an operation display control program stored in the internal memory.

For example, the operation display controller 11 outputs a display signal to the touch panel 13, thereby causing the touch panel 13 to display an operation button and various images. Besides, the operation display controller 11 determines, on the basis of an operation signal output by the operation key 12 or the touch panel 13, which of the operation key 12 and the operation button displayed in the touch panel 13 is operated, and outputs an operation result signal to the arithmetic and control unit 6 on the basis of the result of the determination.

The operation displaying section 1 physically includes the operation key 12 as the hardware key. The operation key 12 is, for example, a power key, a start key, a stop/clear key or a numeric key. If such a key (the operation key 12) is pressed by a user, an operation signal is output from this key (the operation key 12) to the operation display controller 11.

The touch panel 13 includes a display panel, and a transparent sheet pressure sensor (such as a resistive film type sensor) provided on a display surface of the display panel. On the basis of a display signal output by the operation display controller 11, the operation button is displayed in the display panel. If the operation button is pressed by a finger of a user or the like, the sheet pressure sensor outputs an operation signal corresponding to the pressed position (the pressed coordinate) to the operation display controller 11.

Figure 2:
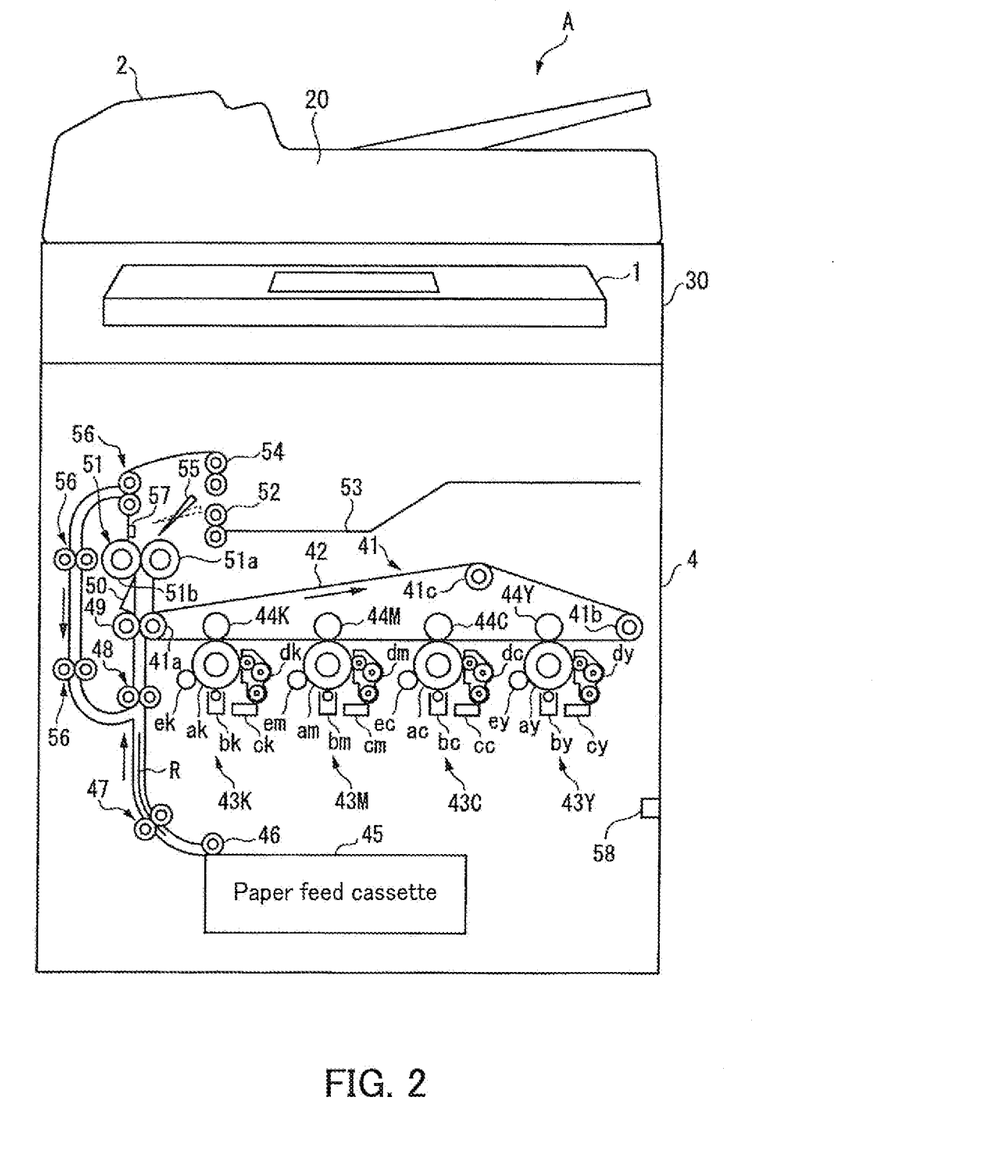
FIG. 2 is a diagram illustrating the configuration of an image forming section of the embodiment.

The image reading section 2 includes, as illustrated in FIG. 2, an ADF (Automatic Document Feeder) 20 and a flatbed reader 30. The ADF 20 feeds an original document to the flatbed reader 30 on the basis of a control signal output by the arithmetic and control unit 6. Alternatively, a user may place an original document on the flatbed reader 30. The image reading section 2 reads a surface image (an original image) of an original document put on the flatbed reader 30, converts the read image into original image data, and outputs the original image data to the image data storing section 3.

The image data storing section 3 is configured by, for example, a semiconductor memory or a hard disk drive. The image data storing section 3 stores image data on the basis of a control signal output by the arithmetic and control unit 6. The image data stored by the image data storing section 3 is, for example, original image data, print image data, or facsimile image data. The communication section 5 receives print image data from an external client computer or facsimile image data from an external facsimile machine. The image forming section 4 reads image data stored in the image data storing section 3 on the basis of a control signal output by the arithmetic and control unit 6.

The image forming section 4 takes out recording paper R from a paper feed cassette 45 and forms an image on the recording paper R on the basis of a control signal output by the arithmetic and control unit 6. The image forming section 4 forms, on the recording paper R, a toner image based on the image data read from the image data storing section 3. The image forming section 4 includes, as illustrated in FIG. 2, belt rollers 41, an intermediate transfer belt 42, image forming units 43Y, 43C, 43M and 43K, primary transfer rollers 44Y, 44C, 44M and 44K, the paper feed cassette 45, a pickup roller 46, conveyor rollers 47, registration rollers 48, a secondary transfer roller 49, a separation discharge portion 50, fixing rollers 51, exit rollers 52, an exit tray 53, inversion rollers 54, a branch guide 55, three pairs of inverted paper feed rollers 56, a recording paper sensor 57 and a humidity detection unit 58. The image forming units 43Y, 43C, 43M and 43K and the primary transfer rollers 44Y, 44C, 44M and 44K are provided respectively correspondingly to toners of four colors (Y, M, C and K). Hereinafter, if there is no need to distinguish them (namely, if common properties and the like are described), each of the image forming units 43Y, 43C, 43M and 43K is designated as the image forming unit 43, and each of the primary rollers 44Y, 44C, 44M and 44 K is designated as the primary transfer roller 44.

The belt rollers 41 include, as illustrated in FIG. 2, three rollers (i.e., a drive roller 41a, a driven roller 41b and a tension roller 41c) provided at a distance. The drive roller 41a and the driven roller 41b are provided at a given distance in the horizontal direction. The tension roller 41c is provided in a position between the drive roller 41a and the driven roller 41b and slightly above the drive roller 41a and the driven roller 41*b*. The intermediate transfer belt 42 is an endless belt stretched around the belt rollers 41 (i.e., the drive roller 41*a*, the driven roller 41*b* and the tension roller 41*c*). The intermediate transfer belt 42 is rotated by the drive roller 41*a* in a direction illustrated with an arrow in FIG. 2. Between the drive roller 41*a* and the driven roller 41*b*, the intermediate transfer belt 42 runs substantially horizontally.

The drive roller 41*a* is connected to, for example, a rotating shaft of a motor generating a driving force. The drive roller 41*a* rotates the intermediate transfer belt 42 in the direction of the arrow by the power of the motor. The driven roller 41*b* is a free roller provided to be freely rotatable. The driven roller 41*b* guides the intermediate transfer belt 42 in accordance with the power of the drive roller 41*a*. The tension roller 41*c* is provided to have a displaceable rotating shaft. The tension roller 41*c* can be pressed against the intermediate transfer belt 42 with a prescribed urging force. Constant tension (tensile force) can be applied by the tension roller 41*c* to the intermediate transfer belt 42.

The image forming units 43Y, 43C, 43M and 43K are provided, as illustrated in FIG. 2, at a prescribed distance in a horizontal region where the intermediate transfer belt 42 horizontally runs as described above. The image forming units 43Y, 43C, 43M and 43K are arranged in this order from one end (closer to the driven roller 41*b*) in the horizontal region of the intermediate transfer belt 42 to the other end (closer to the drive roller 41*a*). The image forming unit 43Y is a unit forming a yellow (Y) toner image. The image forming unit 43C is a unit forming a cyan (C) toner image. The image forming unit 43M is a unit forming a magenta (M) toner image. The image forming unit 43K is a unit forming a black (K) toner image.

The image forming unit 43Y includes a photoconductive drum a*y*, a charger b*y*, a laser scanning unit c*y*, a developing unit d*y* and a cleaner e*y*. The image forming unit 43C includes a photoconductive drum a*c*, a charger b*c*, a laser scanning unit c*c*, a developing unit d*c* and a cleaner e*c*. The image forming unit 43M includes a photoconductive drum a*m*, a charger b*m*, a laser scanning unit c*m*, a developing unit d*m* and a cleaner e*m*. The image forming unit 43K includes a photoconductive drum a*k*, a charger b*k*, a laser scanning unit c*k*, a developing unit d*k* and a cleaner e*k*. Hereinafter, if there is no need to distinguish them (namely, if common properties and the like are described), each of the photoconductive drums a*y*, a*c*, a*m* and a*k* is designated as the photoconductive drum a, each of the chargers b*y*, b*c*, b*m* and b*k* is designated as the charger b, each of the laser scanning units c*y*, c*c*, c*m* and c*k* is designated as the laser scanning unit c, each of the developing units d*y*, d*c*, d*m* and d*k* is designated as the developing unit d, and each of the cleaners e*y*, e*c*, e*m* and e*k* is designated as the cleaner e.

The photoconductive drum a is a cylindrical member having a prescribed photoconductor on its circumferential surface. The photoconductor is made of, for example, amorphous silicon. The charger b is a device for charging the circumferential surface (i.e., the photoconductive surface) of the corresponding photoconductive drum a. The charger b is disposed, for example, so that the circumferential surface of the corresponding photoconductive drum a can be uniformly charged. The laser scanning unit c is a device for forming an electrostatic latent image on the photoconductive surface by irradiating, with laser light, the photoconductive surface having been charged.

The developing unit d contains a prescribed amount of toner (positive toner) therein for supplying the toner to the photoconductive surface. Thus, the electrostatic latent image formed on the photoconductive surface can be developed as a toner image. The cleaner e is a device for removing, by scraping off, the toner remaining on the photoconductive surface (i.e., remaining toner) after transferring the toner image.

The four primary transfer rollers 44Y, 44C, 44M and 44K are provided, as illustrated in FIG. 2, respectively correspondingly to the four image forming units 43Y, 43C, 43M and 43K. The primary transfer rollers 44Y, 44C, 44M and 44K are arranged so as to respectively oppose the photoconductive drums a*y*, a*c*, a*m* and a*k* of the image forming units 43Y, 43C, 43M and 43K with the intermediate transfer belt 42 sandwiched therebetween.

A negative primary transfer bias (a high voltage) is applied to each primary transfer roller 44. The primary transfer belt 44 transfers (primarily transfers) the toner image of the corresponding color having been formed on the photoconductive drum a of the corresponding image forming unit 43 onto the intermediate transfer belt 42 by the function of the primary transfer bias.

The paper feed cassette 45 is a container for containing a pile of a plurality of recording paper R in a prescribed shape (for example, of the A4 size or B5 size). The pickup roller 46 is provided above the paper feed cassette 45 to be in contact with the recording paper R with a pressure. The pickup roller 46 picks up the recording paper R contained in the paper feed cassette 45 one by one and feeds the picked paper to the conveyor rollers 47. The conveyor rollers 47 convey the recording paper R fed from the pickup roller 46 toward the registration rollers 48. The registration rollers 48 supply the recording paper R fed from the conveyor rollers 47 to the secondary transfer roller 49 at a prescribed timing.

The secondary transfer roller 49 is disposed to oppose the drive roller 41*a* with the intermediate transfer belt 42 sandwiched therebetween. The secondary transfer roller 49 transfers (secondarily transfers) the toner image having been transferred to the intermediate transfer belt 42 to the recording paper R. A negative secondary transfer bias (a high voltage) is applied to the secondary transfer roller 49. The secondary transfer roller 49 transfers (secondarily transfers) the toner image formed on the intermediate transfer belt 42 to the recording paper R by the function of the secondary transfer bias.

The separation discharge portion 50 supplies a positive discharging bias to the recording paper R on the basis of a control signal output by the arithmetic and control unit 6. When the discharging bias is applied to the recording paper R, the charge of the recording paper R is neutralized and hence the recording paper R is placed in a non-charged state. Thus, the recording paper R can be suitably separated from the secondary transfer roller 49. The separation discharge portion 50 has a saw-tooth shaped electrode of stainless steel. The separation discharge portion 50 discharges the recording paper R by forming an electric field in the vicinity of the tip of the saw-tooth shaped electrode.

The fixing rollers 51 include a heating roller 51*a* having a heater provided therein and a pressure roller 51*b* in contact with the heating roller 51*a* with a pressure. The fixing rollers 51 heat and press the recording paper R onto which the toner images of the respective colors have been transferred by holding the recording paper R between the heating roller 51*a* and the pressure roller 51*b*. Thus, the toner images of the respective colors are fixed on the recording paper R. The contact surface (the front surface) of each of the heating roller 51*a* and the pressure roller 51*b* to be brought into contact with the recording paper R is made of a fluorine material. The surfaces (i.e., the fluorine materials) of the heating roller 51a and the pressure roller 51b are negatively charged through friction with the recording paper R.

The recording paper R is guided from the fixing rollers 51 by the branch guide 55 to be conveyed to the exit rollers 52 or the inversion rollers 54. The branch guide 55 selectively switches, on the basis of a control signal output by the arithmetic and control unit 6, rollers for feeding the recording paper R having passed through the fixing rollers 51 between the exit rollers 52 and the inversion rollers 54. For example, if the recording paper R is to be conveyed to the exit tray 53, the branch guide 55 is placed in a first attitude (illustrated with a broken line in FIG. 2) so as to feed the recording paper R to the exit rollers 52. On the other hand, if the recording paper R is to be conveyed to the inverted paper feed rollers 56, the branch guide 55 is placed in a second attitude (illustrated with a solid line in FIG. 2) so as to feed the recording paper R to the inversion rollers 54.

The exit rollers 52 convey the recording paper R to the exit tray 53. The exit tray 53 is a container for containing/holding the recording paper R supplied from the exit rollers 52.

The inversion rollers 54 are normally rotated for catching the recording paper R supplied from the fixing rollers 51 and then inversely rotated with the recording paper R caught, so as to convey (switch-back convey) the recording paper R toward the inverted paper feed rollers 56.

On a conveyance path for conveying the recording paper R supplied from the inversion rollers 54 toward the registration rollers 48 (i.e., an inverted conveyance path), a plurality of (three, for example) inverted paper feed rollers 56 are provided. The inverted paper feed rollers 56 are provided, as illustrated in FIG. 2, in three positions spaced from one another on the inverted conveyance path.

The recording paper sensor 57 is provided between the fixing rollers 51 and the branch guide 55. The recording paper sensor 57 detects the number of recording paper R passing through the fixing rollers 51 and outputs a detection signal corresponding to the detected number to the arithmetic and control unit 6.

Owing to the inversion rollers 54, the branch guide 55 and the inverted paper feed rollers 56, duplex image forming processing for forming toner images on a front surface and a rear surface of the recording paper R can be executed in the image forming section 4. For example, recording paper R having an image formed on its front surface passes through the fixing rollers 51 and then is supplied again to the registration rollers 48 after turning the recording paper R over. In this manner, an image can be formed also on the rear surface of the recording paper R.

Figure 3:
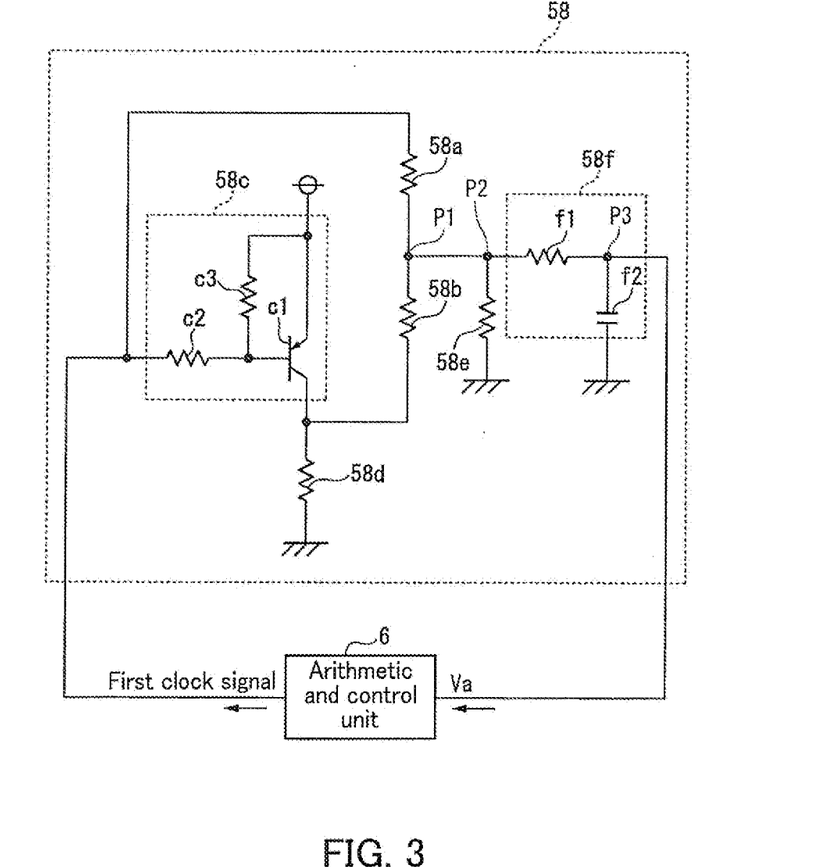
FIG. 3 is a diagram illustrating a circuit including an arithmetic and control unit and a humidity detection unit of the embodiment.

The humidity detection unit 58 is a device for detecting a humidity within a housing the multifunction peripheral A. As illustrated in FIG. 3, the humidity detection unit 58 includes a humidity sensor element 58a, a voltage dividing resistor 58b (a fixed resistor), a clock conversion circuit 58c, a first resistor 58d, a second resistor 58e, and a differentiating circuit 58f.

The humidity sensor element 58a is a resistance changeable humidity sensor element. The humidity sensor element 58a includes an insulating substrate, a pair of electrodes (hereinafter referred to as the first electrode and the second electrode) formed on the insulating substrate, and a moisture sensitive film. The moisture sensitive film is in contact with both the first electrode and the second electrode, and the first electrode is electrically connected to the second electrode via the moisture sensitive film. Therefore, an electric resistance value between the first electrode and the second electrode depends upon the electric resistance value of the moisture sensitive film. The insulating substrate is, for example, an alumina substrate. The moisture sensitive film is made of a moisture sensitive material (such as a polymer). The electric resistance value of the moisture sensitive film is varied in accordance with humidity change. The humidity sensor element 58a changes the electric resistance value between the first electrode and the second electrode in accordance with the humidity change.

The humidity sensor element 58a is produced, for example, as follows. First, an alumina substrate is prepared. Subsequently, a conductive material (such as gold or ruthenium oxide) is printed in a comb shape on the alumina substrate, and the resultant is baked. In this manner, a pair of electrodes opposing each other (for example, a pair of comb shaped electrodes having teeth alternately arranged) are formed on the alumina substrate. Thereafter, a moisture sensitive film is formed on the pair of electrodes by applying, for example, a polymer material.

The humidity sensor element 58a has a first terminal including the first electrode and a second terminal including the second electrode. The first terminal of the humidity sensor element 58a is electrically connected to the output port of the arithmetic and control unit 6, and the second terminal of the humidity sensor element 58a is electrically connected to a terminal (a third terminal described later) of the voltage dividing resistor 58b.

The voltage dividing resistor 58b has a pair of terminals (hereinafter referred to as the third terminal and the fourth terminal). The third terminal of the voltage dividing resistor 58b is electrically connected to the second terminal of the humidity sensor element 58a. The fourth terminal of the voltage dividing resistor 58b is electrically connected to the collector terminal of a switching element c1 of the clock conversion circuit 58c described later and is also electrically connected to the ground via the first resistor 58d. The voltage dividing resistor 58b has a prescribed electric resistance between the third terminal and the fourth terminal. The voltage dividing resistor 58b may be a resistor capable of changing its electric resistance or a resistor incapable of changing its electric resistance. Hereinafter, a node between the second terminal of the humidity sensor element 58a and the third terminal of the voltage dividing resistor 58b is designated as a node P1.

In the humidity detection unit 58, a potential between the second terminal of the humidity sensor element 58a and the third terminal of the voltage dividing resistor 58b (for example, a potential on the node P1) corresponds to a divided voltage value obtained by the humidity sensor element 58a and the voltage dividing resistor 58b (hereinafter referred to as the resistor divided voltage value). The resistor divided voltage value is varied in accordance with the change of the electric resistance value of the moisture sensitive film (or the humidity). Therefore, the resistor divided voltage value corresponds to the humidity.

The clock conversion circuit 58c includes the switching element c1, a third resistor c2 and a fourth resistor c3. The switching element c1 is, for example, a bipolar transistor.

The base terminal of the switching element c1 is electrically connected to the output port of the arithmetic and control unit 6 via the third resistor c2 and is electrically connected also to the first terminal of the humidity sensor element 58a via the third resistor c2. The third resistor c2 is provided for adjusting a current value of a first clock signal input to the base terminal of the switching element c1. The first clock signal is a rectangular wave in which a first level (a high level) and a second level (a low level) are alternately repeated. The first clock signal is, however, not limited to this, but the waveform of the first clock signal is arbitrary and may be, for example, a sine wave, a triangular wave or a sawtooth wave.

The emitter terminal of the switching element c1 is electrically connected to a DC power supply. Besides, the base terminal and the emitter terminal of the switching element c1 are electrically connected to each other via the fourth resistor c3. The fourth resistor c3 is provided for preventing a leakage current or a noise from entering the base terminal of the switching element c1.

The collector terminal of the switching element c1 is electrically connected to the fourth terminal of the voltage dividing resistor 58b and is electrically connected also to the ground via the first resistor 58d.

The switching element c1 outputs, to the fourth terminal of the voltage dividing resistor 58b, a clock signal (a second clock signal) having a phase opposite to that of the clock signal (the first clock signal) output by the arithmetic and control unit 6. The switching element c1 is not limited to a bipolar transistor but may be, for example, an FET (Field Effect Transistor) or an IGBT (Insulated Gate Bipolar Transistor).

The differentiating circuit 58f includes a fifth resistor f1 and a capacitor f2. The differentiating circuit 58f executes differentiation processing (time derivative processing) on the voltage value (resistor divided voltage value) divided between the humidity sensor element 58a and the voltage dividing resistor 58b, and outputs the divided voltage value having been subjected to the differentiation processing (hereinafter referred to as the humidity detection signal Va) to the input port of the arithmetic and control unit 6.

The fifth resistor f1 has a pair of terminals, and one of the terminals (corresponding to a node P2) is electrically connected to the node P1, and the other terminal (corresponding to a node P3) is electrically connected to the input port of the arithmetic and control unit 6. Besides, one of the terminals (corresponding to the node P2) of the fifth resistor f1 is electrically connected to the ground via the second resistor 58e, and the other terminal (corresponding to the node P3) of the fifth resistor f1 is electrically connected to the ground via the capacitor f2.

The communication section 5 communicates, on the basis of a control signal output by the arithmetic and control unit 6, with an external multifunction peripheral or facsimile machine through a telephone line or with a client computer or the like through a LAN (Local Area Network). The communication section 5 has both a communication function in accordance with LAN standards such as Ethernet (registered trademark) and a communication function in accordance with facsimile standards such as G3.

The arithmetic and control unit 6 includes a CPU (Central Processing Unit), a ROM (Read Only Memory), a RAM (Random Access Memory), a storage (such as a hard disk), and an interface circuit. The interface circuit is provided for transmitting/receiving various signals to/from various components electrically connected to the arithmetic and control unit 6 (such as the image forming section 4 of FIG. 1 and the like). The arithmetic and control unit 6 controls the operation of the multifunction peripheral A by performing various arithmetic processing and communications with the respective components on the basis of various arithmetic and control programs stored in the ROM. Besides, the arithmetic and control unit 6 determines, on the basis of the humidity detection signal Va, whether or not the humidity sensor element 58a has a malfunction.

Next, the operation of the multifunction peripheral A having the aforementioned configuration will be described.

For example, for copying an original document by using the multifunction peripheral A, a user sets an original document in the ADF 20. Subsequently, the user instructs the multifunction peripheral A to perform a copying operation (to make, for example, a single-side copy) by operating the operation displaying section 1. The operation displaying section 1 generates an instruction signal corresponding to the content of the instruction issued by the user. The instruction signal is output from the operation displaying section 1 to the arithmetic and control unit 6. When the arithmetic and control unit 6 receives the instruction signal, it causes the image reading section 2 to read an original image on every page of the original document, and causes the image data storing section 3 to store original image data of the read original image. Besides, the arithmetic and control unit 6 generates bitmap image data corresponding to each toner color on the basis of the original image data, and causes the image forming section 4 to execute image forming processing for the original image on the basis of the bitmap image data.

The arithmetic and control unit 6 drives the pickup roller 46 and the conveyor rollers 47 to convey recording paper R held in the paper feed cassette 45 to the registration rollers 48. The pickup roller 46 takes out the recording paper R held in the paper feed cassette 45 one by one and feeds every recording paper R toward the conveyor rollers 47. The conveyor rollers 47 feed the recording paper R toward the registration rollers 48.

Besides, the arithmetic and control unit 6 drives the respective image forming units 43, the drive roller 41a and the registration rollers 48 to transfer a toner image (an original image) onto the recording paper R. Specifically, each image forming unit 43 forms a toner image of a positive toner of the corresponding color on the photoconductive surface (the circumferential surface) of the corresponding photoconductive drum a on the basis of the bitmap image data. Then, the arithmetic and control unit 6 drives the drive roller 41a to rotate the intermediate transfer belt 42, and applies a negative primary transfer bias to each primary transfer roller 44. The arithmetic and control unit 6 controls the operations of the intermediate transfer belt 42 and each primary transfer roller 44, so that the toner images on the respective photoconductive drums a can be primarily transferred onto the intermediate transfer belt 42. Furthermore, the arithmetic and control unit 6 drives the registration rollers 48 in exact timing with the image forming processing for the respective colors performed in the respective image forming units 43. Besides, the arithmetic and control unit 6 applies a negative secondary transfer bias to the secondary transfer roller 49. The arithmetic and control unit 6 controls the operations of the registration rollers 48 and the secondary transfer roller 49, so that the toner image (the original image) on the intermediate transfer belt 42 can be secondarily transferred to a desired position on the recording paper R.

Furthermore, the arithmetic and control unit 6 drives the separation discharge portion 50, the fixing rollers 51, the branch guide 55 and the exit rollers 52, so as to perform a discharging operation, a fixing operation and a paper exiting operation. Specifically, the separation discharge portion 50 discharges the recording paper R with a positive discharging bias. The fixing rollers 51 fix the toner image on the recording paper R. The arithmetic and control unit 6 switches the branch guide 55 to the first attitude (illustrated with a broken line in FIG. 2) for conveying the recording paper R toward the exit rollers 52. Then, the fixing rollers 51 are rotated to convey the recording paper R to the exit rollers 52, and the exit rollers 52 causes the recoding paper R to exit to the exit tray 53.

On the other hand, if a user instructs the multifunction peripheral A to make a double-side copy, after forming an image on the front surface of the recording paper R, the arithmetic and control unit 6 executes the switch-back conveyance for forming an image also on the rear surface of the recording paper R. Specifically, in the same manner as in making a single-side copy as described above, a toner image is fixed on one surface (a front surface) of recording paper R, and thereafter, the arithmetic and control unit 6 switches the branch guide 55 to the second attitude (illustrated with a solid line in FIG. 2) for conveying the recording paper R to the inversion rollers 54. Then, the fixing rollers 51 are rotated to feed the recording paper R to the inversion rollers 54, and the arithmetic and control unit 6 causes the inversion rollers 54 to normally rotate for a prescribed period of time, and then switches the branch guide 55 to the first attitude. Besides, the arithmetic and control unit 6 causes the inversion rollers 54 to inversely rotate for conveying the recording paper R toward the inverted paper feed rollers 56. Then, since the inversion rollers 54 are inversely rotated, the recording paper R is fed to the inverted paper feed rollers 56. Subsequently, the arithmetic and control unit 6 drives the inverted paper feed rollers 56 to feed the recording paper R to the registration rollers 48. Then, the arithmetic and control unit 6 forms an image also on the rear surface of the recording paper R in the same manner as in the image formation on the front surface of the recording paper R.

The arithmetic and control unit 6 detects a humidity within the housing of the multifunction peripheral A in order to, for example, keep the quality of image formation constant. Now, referring to FIG. 4 in addition to FIGS. 1 to 3, a humidity detection method performed by the arithmetic and control unit 6 will be described.

First, in order to detect a humidity within the housing of the multifunction peripheral A, the arithmetic and control unit 6 outputs a first clock signal to the humidity detection unit 58 (specifically, to the humidity sensor element 58a and the clock conversion circuit 58c). The first clock signal is, for example, a digital signal having a frequency of 1 kHz, an amplitude of 3.3 V and a duty of 50% (see an upper row of FIG. 4).

The clock conversion circuit 58c switches (opens/closes) the switching element c1 on the basis of the first clock signal. As a result, the second clock signal having a phase opposite to that of the first clock signal is generated on the fourth terminal of the voltage dividing resistor 58b. The second clock signal is, for example, a digital signal as illustrated in a middle row of FIG. 4.

A composite signal (a combined voltage) of the first clock signal and the second clock signal (both of which are voltage signals) is applied to the humidity sensor element 58a and the voltage dividing resistor 58b serially connected to each other (more specifically, between the first terminal of the humidity sensor element 58a and the fourth terminal of the voltage dividing resistor 58b). When the composite signal is applied to the humidity sensor element 58a and the voltage dividing resistor 58b, the composite signal is divided between the humidity sensor element 58a and the voltage dividing resistor 58b. Thus, a resistor divided voltage value is generated on the node P1. The resistor divided voltage value is differentiated by the differentiating circuit 58f into a humidity detection signal Va. As a result, the humidity detection signal Va is generated on the node P3. The humidity detection signal Va is input to the arithmetic and control unit 6. The humidity detection signal Va input to the arithmetic and control unit 6 is, for example, a signal having a waveform as illustrated in a lower row of FIG. 4.

When the humidity detection signal Va is received, the arithmetic and control unit 6 detects a humidity within the housing of the multifunction peripheral A on the basis of the humidity detection signal Va. Specifically, the arithmetic and control unit 6 acquires the humidity detection signal Va at a timing t1 (corresponding to a first timing) when "(1/a)×L" (wherein a represents a constant larger than 1, and L represents a pulse time width) has elapsed after a rising edge of the first clock signal. Hereinafter, a humidity detection signal Va acquired at the timing t1 is designated as a first resistor divided voltage value Vr.

Figure 5:
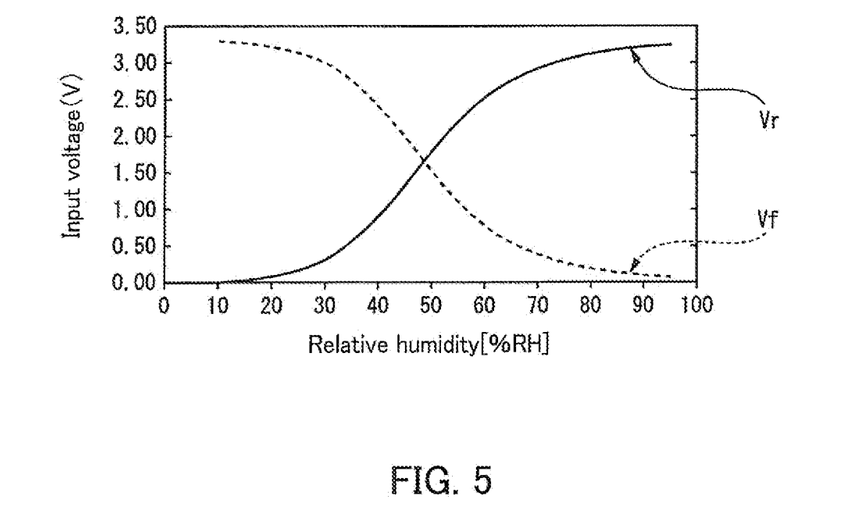
FIG. 5 is a graph of a first resistor divided voltage value and a second resistor divided voltage value used in the embodiment.

The arithmetic and control unit 6 can detect the humidity within the housing of the multifunction peripheral A on the basis of, for example, the first resistor divided voltage value Vr. For example, if "a" is "2" and "L" is "500 μs", "(1/a)×L" is "250 μs". In FIG. 5, the first resistor divided voltage value Vr acquired 250 μs after a rising edge of the first clock signal is graphed with a solid line.

The arithmetic and control unit 6 stores data (hereinafter referred to as a detection map) generated on the basis of the graph of FIG. 5 (obtained as, for example, experiment data) therein (for example, in the hard disk), and can detect a humidity within the housing of the multifunction peripheral A on the basis of the first resistor divided voltage value Vr by making reference to the detection map. In the present embodiment, the arithmetic and control unit 6 corresponds to a detection section.

The first resistor divided voltage value Vr is, for example, as illustrated in FIG. 5, increased nearly up to 3.3 V under a high-humidity environment and is lowered nearly to 0 V under a low-humidity environment. Under the high-humidity environment or the low-humidity environment, the first resistor divided voltage value Vr slightly changes. Therefore, under the high-humidity environment or the low-humidity environment, it is difficult to determine, by using the first resistor divided voltage value Vr alone, whether or not the humidity sensor element 58a has a malfunction.

The arithmetic and control unit 6 acquires a resistor divided voltage value Va at a timing t2 (corresponding to a second timing) when "(1/a)×L" (wherein a represents a constant larger than 1, and L represents a pulse time width) has elapsed after a falling edge of the first clock signal. Hereinafter, a humidity detection signal Va acquired at the timing t2 is designated as a second resistor divided voltage value Vf. Incidentally, the arithmetic and control unit 6 may always (continuously) acquire the second resistor divided voltage value Vf or acquire the second resistor divided voltage value Vf every prescribed time period (intermittently).

In FIG. 5, the second resistor divided voltage value Vf acquired 250 μs after a falling edge of the first clock signal is graphed with a broken line. As illustrated in FIG. 5, under either a high-humidity environment or a low-humidity environment, there is a large difference between the first resistor divided voltage value Vr and the second resistor divided voltage value Vf. Therefore, it is possible to highly precisely detect a malfunction of the humidity sensor element 58a by comparing the first resistor divided voltage value Vr and the second resistor divided voltage value Vf with each other. For example, if a difference or a ratio between the first resistor divided voltage value Vr and the second resistor divided voltage value Vf does not fall in a prescribed range (namely, does not have a normal value), it can be determined that the humidity sensor element 58a has a malfunction.

Figure 4:
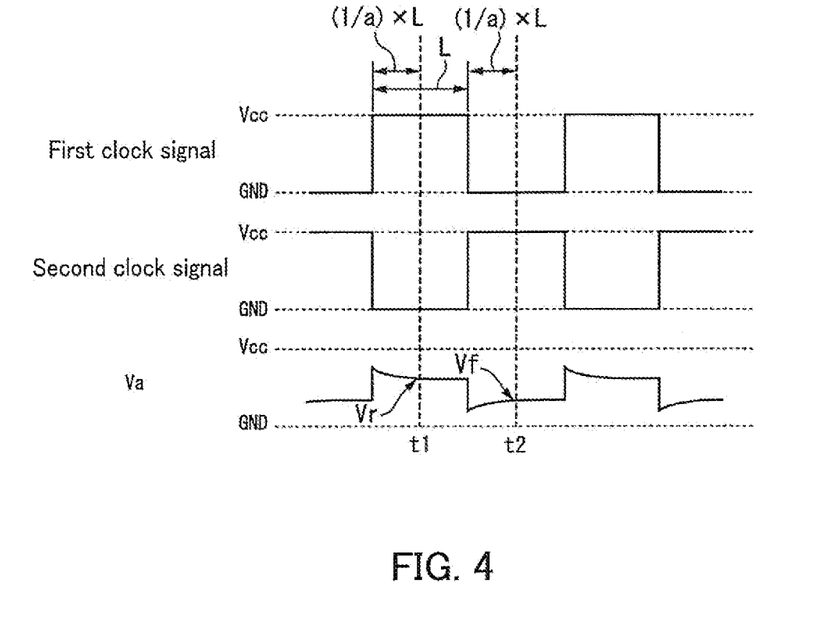
FIG. 4 is a diagram of waveforms (transitions of voltage values) of a first clock signal, a second clock signal and a humidity detection signal used in the embodiment.

Now, mainly referring to FIGS. 4 and 5, an example of a method for detecting a malfunction of the humidity sensor element 58a by the arithmetic and control unit 6 will be described.

First, examples of the first resistor divided voltage value Vr and the second resistor divided voltage value Vf obtained when the humidity sensor element 58a is normal will be described. If the humidity sensor element 58a is normal, as illustrated in FIG. 5 for example, the first resistor divided voltage value Vr is larger as the humidity is higher, and the second resistor divided voltage value Vf is smaller as the humidity is higher.

Next, examples of the first resistor divided voltage value Vr and the second resistor divided voltage value Vf obtained when the humidity sensor element 58a has a malfunction will be described. If the humidity sensor element 58a has a malfunction, no voltage is applied to the voltage dividing resistor 58b at the timing t1 when "(1/a)×L" has elapsed after a rising edge of the first clock signal, and hence, the first resistor divided voltage value Vr is 0 V. On the other hand, the second clock signal at a high level is applied to the voltage dividing resistor 58b at the timing t2 when "(1/a)×L" has elapsed after a falling edge of the first clock signal, and hence, the second resistor divided voltage value Vf is 3.3 V.

In the above-described example, if the humidity sensor element 58a has a malfunction, a value obtained by subtracting the second resistor divided voltage value Vf from the first resistor divided voltage value Vr (i.e., Vr−Vf) is always −3.3 V. On the other hand, if the humidity sensor element 58a is normal, it is merely when the humidity is extremely low that the value "Vr−Vf" is −3.3 V (see FIG. 5). Therefore, under a general use environment, it is presumed that abnormality of the value "Vr−Vf" (in other words, a malfunction of the humidity sensor element 58a) can be easily detected. The arithmetic and control unit 6 can determine whether or not the humidity sensor element 58a has a malfunction by utilizing the aforementioned characteristics of the first resistor divided voltage value Vr and the second resistor divided voltage value Vf.

Next, mainly referring to FIGS. 4 and 5, an example of a method for detecting a malfunction of the clock conversion circuit 58c by the arithmetic and control unit 6 will be described.

First, examples of the first resistor divided voltage value Vr and the second resistor divided voltage value Vf obtained when the clock conversion circuit 58c has a malfunction will be described. If the clock conversion circuit 58c has a malfunction, the first resistor divided voltage value Vr has a value according to the ambient humidity at the timing t1 when "(1/a)×L" has elapsed after a rising edge of the first clock signal. On the other hand, at the timing t2 when "(1/a)×L" has elapsed after a falling edge of the first clock signal, no voltage is applied to the voltage dividing resistor 58b, and hence the second resistor divided voltage value Vf is 0 V.

In the aforementioned example, if the humidity sensor element 58a has a malfunction, a value obtained by subtracting the second resistor divided voltage value Vf from the first resistor divided voltage value Vr (i.e., Vr−Vf) always accords with the first resistor divided voltage value Vr. On the other hand, if the humidity sensor element 58a is normal, it is merely when the humidity is extremely high that the value "Vr−Vf" accords with the first resistor divided voltage value (see FIG. 5). Therefore, under a general use environment, it is presumed that abnormality of the value "Vr−Vf" (in other words, a malfunction of the clock conversion circuit 58c) can be easily detected. The arithmetic and control unit 6 can determine whether or not the clock conversion circuit 58c has a malfunction by utilizing the aforementioned characteristics of the first resistor divided voltage value Vr and the second resistor divided voltage value Vf.

In the multifunction peripheral A (corresponding to an abnormality detection apparatus for a humidity sensor device) of the present embodiment, the arithmetic and control unit 6 (corresponding to the determination section) acquires a humidity detection signal Va (namely, a first resistor divided voltage value Vr) at the timing t1 (namely, a timing within a period from a rising edge to a falling edge of the first clock signal), and acquires a humidity detection signal Va (namely, a second resistor divided voltage value Vf) at the timing t2 (namely, a timing within a period from a falling edge to a rising edge of the first clock signal). Then, the arithmetic and control unit 6 (corresponding to the determination section) determines, on the basis of the first resistor divided voltage value Vr and the second resistor divided voltage value Vf, whether or not a detected humidity value (namely, a humidity detected by the arithmetic and control unit 6) is normal.

Owing to the aforementioned configuration, it is possible to more accurately determine whether or not a detected humidity value is normal in the multifunction peripheral A (corresponding to the abnormality detection apparatus for a humidity sensor device). Besides, in the multifunction peripheral A (corresponding to the abnormality detection apparatus for a humidity sensor device), it is possible to more accurately determine, on the basis of the first resistor divided voltage value Vr and the second resistor divided voltage value Vf, whether or not the humidity sensor element 58a has a malfunction. Furthermore, in the multifunction peripheral A (corresponding to the abnormality detection apparatus for a humidity sensor device), it is possible to more accurately determine, on the basis of the first resistor divided voltage value Vr and the second resistor divided voltage value Vf, whether or not the clock conversion circuit 58c has a malfunction.

The multifunction peripheral A (the abnormality detection apparatus for a humidity sensor device) according to the present embodiment includes a signal processing circuit (specifically, the differentiating circuit 58f) for executing prescribed signal processing (specifically, the differentiation processing) on a resistor divided voltage value. Besides, the arithmetic and control unit 6 (the determination section) acquires, at the timing t1 and the timing t2, a resistor divided voltage value (namely, a humidity detection signal Va) resulting from the signal processing (specifically, the differentiation processing). Then, the arithmetic and control unit 6 (the detection section) determines, on the basis of the humidity detection signal Va, whether or not a detected humidity value (namely, a humidity detected by the arithmetic and control unit 6) is normal. In such a configuration, it is possible to make the waveform dull and to remove noise by executing the differentiation processing on the resistor divided voltage value.

The embodiment of the present disclosure has been described so far, but the present disclosure is not limited to the above embodiment. The present disclosure can be modified, for example, as follows:

Although "2" is substituted for "a" in "(1/a)×L" in the above-described embodiment, "a" is not limited to "2" but can be any value as long as a >1.

In the multifunction peripheral A (namely, the abnormality detection apparatus for a humidity sensor device) according to the above-described embodiment, it is determined, based on the resistor divided voltage value resulting from the differentiation processing (namely, the humidity detection signal Va), whether or not a detected humidity value is normal. The present disclosure is, however, not limited to this, but signal processing other than the differentiation processing (such as integration processing) may be executed on the resistor divided voltage value, or the resistor divided voltage value may not be subjected to the signal processing. For example, the differentiating circuit 58f may be omitted, or an integrating circuit may be provided instead of the differentiating circuit 58f.

Any of a plurality of methods for detecting abnormality may be selectively employed in accordance with the humidity environment (i.e., a humidity range). For example, under at least one of a high-humidity environment (having, for example, a humidity of a prescribed value or higher) and a low-humidity environment (having, for example, a humidity of a prescribed value or lower), the determination whether or not a detected humidity value is normal may be made on the basis of the first resistor divided voltage value Vr and the second resistor divided voltage value Vf, and under the other humidity environment, the determination may be made by another method.

In the above-described embodiment, the arithmetic and control unit 6 may determine, on the basis of a plurality of first resistor divided voltage values Vr and a plurality of second resistor divided voltage values Vf, whether or not a detected humidity value is normal (or whether or not the humidity sensor element 58a or the clock conversion circuit 58c has a malfunction). For example, the arithmetic and control unit 6 may determine, on the basis of an average of a plurality of first resistor divided voltage values Vr and an average of a plurality of resistor divided voltage values Vf, whether or not a detected humidity value is normal (or whether or not the humidity sensor element 58a or the clock conversion circuit 58c has a malfunction).

If it is determined that the detected humidity value is not normal (or the humidity sensor element 58a or the clock conversion circuit 58c has a malfunction), the arithmetic and control unit 6 may inform a user of the determination result. For example, the arithmetic and control unit 6 may display the determination result on a display or may actuate an alarm device for sounding an alarm at the time of abnormality.

What is claimed is:

1. An image forming apparatus, comprising:
   a humidity sensor element having a first terminal and a second terminal, and configured to vary, in accordance with humidity change, an electric resistance value between the first terminal and the second terminal;
   a resistor having a third terminal and a fourth terminal, with the third terminal serially connected to the second terminal, and having a prescribed electric resistance between the third terminal and the fourth terminal;
   a clock supply section configured to supply a first clock signal to the first terminal and a second clock signal having an opposite phase to the first clock signal to the fourth terminal;
   a detection section configured to detect a humidity on the basis of a divided voltage value obtained by the humidity sensor element and the resistor; and
   a determination section configured to acquire the divided voltage value at a first timing within a period from a rising edge to a falling edge of the first clock signal and at a second timing within a period from a falling edge to a rising edge of the first clock signal, and to determine that the humidity sensor element has a malfunction when the divided voltage value acquired at the first timing is a low-level potential value of the first and second clock signals and the divided voltage value acquired at the second timing is a high-level potential value of the first and second clock signals.

2. An image forming apparatus according to claim 1, wherein the clock supply section includes a clock generation circuit generating the first clock signal and a clock conversion circuit generating the second clock signal on the basis of the first clock signal, and
   the determination section determines that the clock conversion circuit has a malfunction when the divided voltage value acquired at the first timing is a potential value other than the low-level potential value of the first and second clock signals and the divided voltage value acquired at the second timing is the low-level potential value of the first and second clock signals.

3. An image forming apparatus according to claim 1, wherein the determination section determines, on the basis of a plurality of divided voltage values acquired at the first timing and a plurality of divided voltage values acquired at the second timing, whether or not the humidity detected by the detection section is normal.

4. An image forming apparatus according to claim 1, wherein the determination section acquires the divided voltage value at the second timing every prescribed time period.

5. An image forming apparatus according to claim 1, wherein the determination section always acquires the divided voltage value at the second timing.

6. An image forming apparatus according to claim 1, further comprising a signal processing circuit executing prescribed signal processing on the divided voltage value,
   wherein the determination section acquires, at the first timing and the second timing, the divided voltage value having been subjected to the prescribed signal processing, and determines, on the basis of the divided voltage value having been subjected to the prescribed signal processing, whether or not the humidity detected by the detection section is normal.

7. An image forming apparatus according to claim 6, wherein the signal processing is differentiation processing and the signal processing circuit is a differentiating circuit.

8. An abnormality detection apparatus for a humidity sensor device for detecting whether or not the humidity sensor device has abnormality,
   the humidity sensor device including:
      a humidity sensor element having a first terminal and a second terminal, and configured to vary, in accordance with humidity change, an electric resistance value between the first terminal and the second terminal;
      a resistor having a third terminal and a fourth terminal, with the third terminal serially connected to the second terminal, and having a prescribed electric resistance between the third terminal and the fourth terminal;
      a clock supply section configured to supply a first clock signal to the first terminal and a second clock signal having an opposite phase to the first clock signal to the fourth terminal; and
      a detection section configured to detect a humidity on the basis of a divided voltage value obtained by the humidity sensor element and the resistor,
   the abnormality detection apparatus for a humidity sensor device, comprising a determination section configured to acquire the divided voltage value at a first timing within a period from a rising edge to a falling edge of the first clock signal and at a second timing within a period from a falling edge to a rising edge of the first clock signal, and to determine that the humidity sensor element has a malfunction when the divided voltage value acquired at the first timing is a low-level potential value of the first and second clock signals and the divided voltage value acquired at the second timing is a high-level potential value of the first and second clock signals.

9. An abnormality detection method for a humidity sensor device for detecting whether or not the humidity sensor device has abnormality, the humidity sensor device including:
  a humidity sensor element having a first terminal and a second terminal, and configured to vary, in accordance with humidity change, an electric resistance value between the first terminal and the second terminal;
  a resistor having a third terminal and a fourth terminal, with the third terminal serially connected to the second terminal, and having a prescribed electric resistance between the third terminal and the fourth terminal;
  a clock supply section configured to supply a first clock signal to the first terminal and a second clock signal having an opposite phase to the first clock signal to the fourth terminal; and
  a detection section configured to detect a humidity on the basis of a divided voltage value obtained by the humidity sensor element and the resistor, the method comprising:

acquiring the divided voltage value at a first timing within a period from a rising edge to a falling edge of the first clock signal;

acquiring the divided voltage value at a second timing within a period from a falling edge to a rising edge of the first clock signal; and determining that the humidity sensor element has a malfunction when the divided voltage value acquired at the first timing is a low-level potential value of the first and second clock signals and the divided voltage value acquired at the second timing is a high-level potential value of the first and second clock signals.

* * * * *